United States Patent [19]

Lundin et al.

[11] Patent Number: 4,859,794

[45] Date of Patent: Aug. 22, 1989

[54] PERESTERS, THEIR PREPARATION AND USE AS POLYMERIZATION INITIATORS

[75] Inventors: Claes O. A. Lundin, Saltsjö-Boo; Erik M. Larsson, Stockholm; Björn J. E. Akermark, Saltsjöbaden, all of Sweden

[73] Assignee: Berol Nobel Nacka AB, Stockholm, Sweden

[21] Appl. No.: 128,167

[22] Filed: Dec. 3, 1987

[30] Foreign Application Priority Data

Dec. 8, 1986 [SE] Sweden ................. 8605242

[51] Int. Cl.$^4$ ............................................ C07C 179/18
[52] U.S. Cl. .................................................... 560/302
[58] Field of Search ......................................... 560/302

[56] References Cited

U.S. PATENT DOCUMENTS 2,608,571  8/1952  Rust ................................... 560/302

FOREIGN PATENT DOCUMENTS 0095860  12/1983  European Pat. Off. .

OTHER PUBLICATIONS

*Chem. Abstracts*, 104:225267h, "Initiation of Radical Reactions by Thermal . . . " (1986).

*Primary Examiner*—Bruce Gray
*Attorney, Agent, or Firm*—Burns, Doane, Swecker & Mathis

[57] ABSTRACT

New dialkyl esters of monoperoxyoxalic acid which have a tertiary alkyl group in the perester part of the molecule while the other alkyl group is a long-chain, primary alkyl group. The compounds give rise to radicals at heating and are useful as initiators for the polymerization of ethylenically unsaturated monomers, particularly for the polymerization of vinyl chloride.

2 Claims, No Drawings

PERESTERS, THEIR PREPARATION AND USE AS POLYMERIZATION INITIATORS

The present invention relates to new dialkyl esters of monoperoxyoxalic acid, and more particularly to such compounds wherein the alkyl group in the perester part of the molecule is a tertiary alkyl group while the other alkyl group is a long-chain primary alkyl group. The invention also relates to a method for the preparation of the compounds and to the use of the new compounds as initiators for polymerization of ethylenically unsaturated monomers, particularly for polymerization of vinyl chloride.

Vinyl chloride is usually polymerized in aqueous suspension systems and the polymerization is initiated by thermal decomposition of monomer soluble, radical forming compounds, eg organic peroxides and azo compounds. The polymerization process, which normally is carried out at a constant temperature, is an exothermal process and the reaction heat must be cooled off at the same speed at which it is formed. The most important limiting production factor is thus the cooling capacity of the reactor. The production rate is further limited by the fact that the polymerization reaction accelerates and has its highest heat/power generation at a degree of conversion of 75%. Before this degree of conversion is reached the cooling capacity is incompletely utilized. The total reaction time is influenced by the fact that the highest instantaneous heat/power generation must be adapted to the cooling capacity of the reactor. It is possible to achieve a polymerization with almost constant heat/power generation by using a combination of two or more initiators having different rates of radical formation and hereby the cooling capacity is utilized in a better way and a shorter polymerization time is obtained.

At polymerization of vinyl chloride on an industrial scale moderately active compounds are used to a great extent, such as dialkyl peroxydicarbonates and diacyl peroxides, and here the most common initiators, dicetyl peroxydicarbonate and dilauroyl peroxide, have half lives of 5 to 6 hours at 50° C. and of more than 40 hours at 50° C., respectively. These initiators are advantageous with regard to safety and manageability and are solid at room temperature. The simplest way of increasing productivity at a given cooling capacity is, as stated above, utilization of initiators having a higher rate of decomposition in combination with moderately active initiators. A number of initiators with a higher rate of decomposition exist and as examples of such initiators can be mentioned acetylcyclohexyl sulfonylperoxide which has a half life of about 1.25 hours at 50° C. and cumylperneodecanoate, and these are used in combination with slower initiators. They have, however, not reached any greater commercial use and evidently do not show all the desirable properties for problem-free use.

The present invention relates to new compounds, to certain dialkyl esters of monoperoxyoxalic acid which are suitable as initiators for polymerization of vinyl chloride and other ethylenically unsaturated monomers. Dialkyl esters of monoperoxyoxalic acid are per se known and known for use as polymerization initiators. The European patent application 0095860 discloses dialkyl esters of monoperoxyoxalic acid where the alkyl group in the perester part of the molecule is a secondary or tertiary alkyl group, a benzyl group or a substituted benzyl group while the other alkyl group also is such a group and whereby both groups contain from 4 to 10 carbon atoms and the European patent application relates particularly to di(tert-butyl)monoperoxyoxalate. These compounds certainly have short half lives but they are disadvantageous for example in that they are liquid compounds, having melting points below 0° C., which is an obvious disadvantage with regard to safe transport, storage and manageability. These esters are also disadvantageous in that they give rise to a partial aqueous phase polymerization which can result in an impaired polymer quality.

The present new dialkyl esters of monoperoxyoxalic acid wherein one alkyl group is a long-chain, primary, normal alkyl group have melting points above +5° C. which means that they can be handled as powder when stored in a refrigerator. Most of the compounds are solid at room temperature and can be stored at room temperature for shorter periods of time.

The new compounds according to the present invention are characterized by the general formula

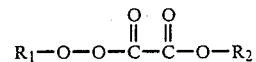

wherein $R_1$ is a tertiary alkyl group having from 4 to 10 carbon atoms and $R_2$ is a primary, normal alkyl group having from 18 to 28 carbon atoms.

The compounds of the invention have melting points above +5° C. and those with melting points above +25° C. are preferred, ie compounds which are solid at room temperature. $R_1$ in the compounds is a tertiary alkyl group having from 4 to 10 carbon atoms, suitably from 4 to 8 carbon atom. As examples of suitable tertiary alkyl groups can be mentioned tertiary butyl, tertiary pentyl, tertiary hexyl, tertiary heptyl, 2,4,4-trimethyl-2-pentyl and 1-methyl-1-cyclohexyl groups. It is particularly preferred that the tertiary alkyl group is a tertiary butyl, tertiary amyl, 2,4,4-trimethyl-2-pentyl or a 1-methyl-1-cyclohexyl group, and the two first mentioned groups are especially preferred.

$R_2$ is a primary, normal, ie straight, alkyl group having at least 18 carbon atoms. This alkyl group can contain up to 28 carbon atoms and preferably it contains from 18 to 24 carbon atoms. The melting point of the compounds is not only dependent on the long-chain alkyl group but also of the tertiary alkyl group on the perester part of the molecule. As some examples of suitable dialkyl esters can be mentioned octadecyl(t-butylperoxy)oxalate, octadecyl(t-pentylperoxy)oxalate, octadecyl(t-hexylperoxy)oxalate, octadecyl(t-heptylperoxy)oxalate, octadecyl(toctylperoxy)oxalate, octadecyl(2,4,4-trimethyl-2-pentylperoxy)oxalate, octadecyl(1-methyl-1-cyclohexylperoxy)oxalate and corresponding compounds wherein the alkyl group in the ester part of the molecule is an eicosyl, docosyl and tetracosyl group respectively. Particularly suitable are octadecyl(t-butylperoxy)oxalate, eicosyl(t-butylperoxy)oxalate, eicosyl(t-pentylperoxy)oxalate, docosyl(t-butylperoxy)oxalate, docosyl(t-pentylperoxy)oxalate, docosyl(t-hexylperoxy)oxalate, docosyl(t-heptylperoxy)oxalate, docosyl(t-octylperoxy)oxalate, docosyl(2,4,4-trimethyl-2-pentylperoxy)oxalate and docosyl(1-methyl-1-cyclohexylperoxy)oxalate.

The fact that the alkyl group in the perester part of the molecule is a tertiary group contributes to an increased stability of the compounds and is a condition for obtaining radical formation at heating. Compared with previously known monoperoxyoxalates the present compounds show a generally improved stability and do not have any explosive properties.

The present dialkyl esters of monoperoxyoxalic acid have somewhat longer half lives than the previously known dialkyl esters which do not contain longer, primary, normal alkyl groups, but shorter half lives than the commercially used moderately active peroxides. However, a not too short half life is advantageous with respect to polymerization since hereby not so much initiator is consumed in the initial stage of the polymerization when the rate of conversion is low due to a high termination. On condition that the initiator is completely consumed, an initiator having a somewhat longer half life gives more polymer per mole initiator. A slower initiator will also get a better distribution in the monomer phase before the actual polymerization starts. Such an initiator is also more stable towards decomposition at the polymerization preparation, addition and deoxygenation, which should be carried out at as high a temperature as possible.

The present new dialkyl esters of monoperoxyoxalic acid are thus, as they are solid compounds at temperatures above +5° C., advantageous with regard to handling and safety and as they, as stated above, have a balanced half life, they are also advantageous with regard to actual polymerization productivity. Further, they have a low water solubility and low vapour pressure which is advantageous with regard to the polymerization process and the properties of the produced polymerizate as this decreases the risk of partial aqueous phase polymerization with resulting crust formation in the reactor and decreases negative influence on the polymerizate such as formation of fish eyes. Further, the chemical constitution of the compounds is such that they do not form decomposition products or residual products which contaminate recovered monomer, process water or finished polymer product.

The new compounds of the invention can be prepared according to principally known manners, eg as disclosed in the European patent application 95860. They can thus be prepared by reacting an alcohol with oxalyl chloride followed by reacting the obtained reaction product with an alkylhydroperoxide, or alternatively by first reacting oxalyl chloride with an alkylhydroperoxide followed by reacting the obtained reaction product, the alkylmonoperoxyoxalyl chloride, with an alcohol. Hereby the alkylhydroperoxide is of course an alkylhydroperoxide of the formula $R_1OOH$ wherein $R_1$ is the tertiary alkyl group as defined for the present compounds and the alcohol has the formula $R_2OH$ wherein $R_2$ is the long-chain, primary, normal alkyl group as defined above. Reactions which include the peroxy compounds are suitably carried out at temperatures below +5° C. and in inert solvents such as aromatic solvents, alkanes and ethers. Reactions which involve alcohol and not peroxy compounds can be carried out at higher temperatures, up to the boiling point of the oxalyl chloride. In order to neutralize hydrochloric acid formed at the reactions a base, eg pyridine, triethylamine or dimethylaminopyridine, can be added to the reaction mixtures. The present invention also relates to a method for preparation of the new compounds whereby oxalyl chloride is reacted with an alkylhydroperoxide $R_1OOH$ and the reaction product subsequently is reacted with an alcohol $R_2OH$, or alternatively first with the alcohol and subsequently with the hydroperoxide, whereby the alkyl groups $R_1$ and $R_2$ have the above given definitions. At reaction between oxalyl chloride and a hydroperoxide an alkylperoxyalkylchloride is obtained as intermediate product. This compound is very reactive and decomposes explosively both at heating and in contact with water. It is thus preferred that the compounds are prepared by reacting an alcohol with oxalyl chloride followed by reacting the intermediate product with an alkylhydroperoxide.

The compounds according to the invention can be used at known methods for polymerization of ethylenically unsaturated monomers and are preferably used for homo- or copolymerization of vinyl chloride. The compounds can be used in conventional processes for vinyl chloride polymerization such as bulk polymerization, suspension- and microsuspension polymerization. The use of the compounds for polymerization of ethylenically unsaturated monomers, preferably for homo- or copolymerization of vinyl chloride forms part of the present invention. As examples of ethylenically unsaturated monomers can be mentioned: vinyl aromatic compounds, eg styrene and substituted styrenes, esters of aliphatic α-methylene carbonic acids, preferably lower alkyl esters such as methylacrylate, ethylacrylate, methyl metacrylate, ethyl methacrylate etc, acrylic acid nitrile, vinyl esters such as vinyl acetate, vinyl halides, vinyl ethers, vinylidene chloride and lower alkenes, etc.

The compounds are preferably used for polyerization of vinyl chloride or vinyl chloride and copolymerizable monomers. At copolymerization of vinyl chloride with other monomers the main part of monomer should be vinyl chloride and suitably not more than 20 per cent by weight of copolymerizable monomers, based on the vinyl chloride, are used. As examples of monomers which are copolymerizable with vinyl chloride can be mentioned alkenes, vinyl acetate, vinylidene chloride, acrylic and methacrylic acid, acrylates and methacrylates, acrylonitrile and methacrylonitrile, vinyl esters etc.

The use of the present compounds as initiators for polymerization of vinyl chloride, or vinyl chloride and copolymerizable compounds, by bulk polymerization or in aqueous systems by suspension- or microsuspension polymerization is thus a preferred embodiment of the present invention. In suspension polymerization a suspension agent, usually a protective colloid, is used and at microsuspension polymerization a surface active agent, an emulsifier and/or a suspension agent is used. At suspension polymerization with the present compounds conventional suspension agents/protective colloids, eg polyvinyl acetate, which can be partially hydrolyzed, polyvinylpyrrolidone, polyacrylic acid, acrylic acid copolymers, water soluble cellulose derivatives, gelatin, starch etc, can be used and be used in conventional amounts. The compounds of the invention are used in per se conventional amounts, ie usually in amounts of from 0.01 to 2 per cent by weight based on the amount of monomer. The polymerization is carried out at conventional pressures and temperatures, usually from 0.5 to 1.5 MPa and from 30° to 70° C., respectively. The initiators can normally be added in solid form, powder form, directly after the optional cool storage. If desired, dispersions of the initiators can be prepared in per se known manners and using per se known dispersing agents, in order to achieve more advantageous conditions of addition. The initiators according to the invention can of course also be used in combination with other initiators and it is particularly advantageous to use the present initiators in combination with slower initiators and hereby obtain both a faster process to constant polymerization rate and a sufficient radical formation at the end of the polymerization process.

At the use as polymerization initiators the compounds are advantageous with regard to handling and safety and can in many cases in these aspects be compared with initiators such as dicetylperoxydicarbonate and dilauroylperoxide. However, in comparison with these they are advantageous in that they have a substantially lower half life. In comparison with previously known initiators having a short half life the present compounds have, as stated above, besides the advantages with regard to handling and safety, also the advantage that they, despite a somewhat longer half life, can give as well good yields during a specified time period since not so much initiator is consumed during the initial stage and as they will reach a better distribution in the monomer phase before the actual polymerization process and as the risk of partial polymerization in the aqueous phase is low due to the fact that the compounds have low water solubility. The cooling capacity of existing reactors can be utilized in the best possible manner with the present initiators, the so-called max-effect peak at the end of the polymerization can be suppressed with simultaneous reduction of the polymerization time. Polymers, such as vinyl chloride polymerizates, prepared using the present initiators, have good properties.

The invention is further illustrated in the following examples, which, however, are not intended to limit the same. Parts and per cent relate to parts by weight and per cent by weight, respectively, unless otherwise stated.

EXAMPLE 1

Synthesis of docosyl(t-butylperoxy)oxalate 16.5 grams of docosanol were dissolved in 950 ml of dried ether and then added drop by drop to a solution of 8.6 ml of oxalyl chloride in 100 ml of dried ether. The mixture was allowed to stand for about 16 hours at room temperature under agitation. The ether and excess of oxalyl chloride were the distilled off under vacuum. The obtained docosyloxalyl chloride, which is a solid, white mass, was then dissolved in 500 ml of pentane and added drop by drop to a solution of 6.7 g of t-butylhydroperoxide and 8.1 g of dimethylaminopyridine in about 90 ml of pentane. The temperature of the reaction mixture was kept at 0° C. during the synthesis. After the addition the mixture was allowed to stand under agitation for about 1.5 hours. The precipitation of aminohydrochloride was filtered off and the filtrate was washed with diluted hydrochloric acid, saturated sodiumbicarbonate and water, in the given order. After drying with magnesium sulphate the solvent was distilled off under vacuum. The yield was 16.9 g of a solid white powder having a content of more than 95% and a melting point of 42° C., measured with DSC. This corresponds to a yield of 70% calculated on the amount of alcohol used. IR-spectrum in carbon tetrachloride gave the characteristic carbonyl-absorptions at 1795 and 1750 cm$^{-1}$. The contents of the product did not decrease during 5 weeks of storage at 5° C. The half life at 50° C. was 2.0 hours and this was measured by IR dissolved in 1,1,1-trichloroethane.

In the same manner the following esters of monoperoxy oxalic acid were prepared (melting point, half life at 50° C.):
docosyl(t-pentylperoxy)oxalate (36° C., 1.5 hours)
docosyl(2,4,4-trimethyl-2-pentylperoxy)oxalate (27° C., 0.7 hours)
docosyl (1-methyl-1-cyclohexylperoxy)oxalate (32° C., 0.8 hours)
eicosyl(t-butylperoxy)oxalate (33° C., 2.0 hours)
eicosyl(t-pentylperoxy)oxalate (26° C., 1.5 hours)
eicosyl(2-methyl-2-hexylperoxy)oxalate (14° C., 1.5 hours)
octadecyl(t-butylperoxy)oxalate (27° C., 2.2 hours)
octadecyl(t-pentylperoxy)oxalate (12° C., 1.5 hours)

All the compounds showed the characteristic carbonyl absorptions.

EXAMPLE 2

The following were added to a 14 l steel autoclave: 6300 g of water, a dispersing agent of PVA-type and 3.74 g of an initiator which was:

Example 2a: Docosyl(t-butylperoxy)oxalate (as solid powder)

Example 2b: Dicetylperoxydicarbonate (as a 20% dispersion in water), comparison.

The speed of agitation in the system was 450 r/min and the temperature 40° C. The autoclave was closed and evacuated. 25 minutes after the addition of the initiator 5500 g of vinyl chloride were added and the autoclave heated to 55° C., which took 25 minutes.

| Results | Ex 2a | Ex 2b |
|---|---|---|
| Time to the start of the pressure drop | 4 hours | 5 hours |
| Time to 700 kPa | 5 hours | 5.5 hours |
| pH of the polymerization slurry | 8.0 | 8.2 |
| Crusts | 0 | 0 |
| Polymer properties | | |
| Volume weight | 460 kg/m$^3$ | 475 kg/m$^3$ |
| Sieve analysis | | |
| >160 μ | 5 g/kg | 10 g/kg |
| 100–160 μ | 530 g/kg | 560 g/kg |
| 63–100 μ | 440 g/kg | 400 g/kg |
| <63 μ | 25 g/kg | 30 g/kg |
| VDE-stability | 93 min | 72 min |
| (time for development of a certain amount of HCl) | | |

EXAMPLE 3

Polymerization of vinyl chloride on a commercial scale was carried out in a 30m$^3$ autoclave. A conventional polymerization recipe was used. The polymerization temperature was 52° C. and the polymerization was run until the pressure in the autoclave had fallen to 650 kPa. In polymerization (a) 0.1 per cent by weight, based on the vinyl chloride, of dicetylperoxydicarbonate was used as initiator and was charged in the form of a dispersion. In polymerization (b) 0.085 per cent by weight, based on vinyl chloride, of docosyl(t-butylperoxy)oxalate was used as initiator and was charged as a solid powder.

The polymerization time, ie the time from reaching the polymerization temperature of 52° C. to a pressure of 650kPa, was for polymerization (a) 5.5 hours and for polymerization (b) 4.25 hours. The obtained vinyl chloride polymerizates had equally good properties with regard to volume weight and porosity.

We claims:

1. Dialkyl esters of monoperoxyoxalic acid, characterized by the general formula
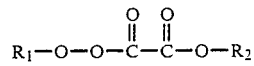
wherein $R_1$ is a tertiary alkyl group having 4 to 10 carbon atoms and $R_2$ is a primary, normal alkyl group having 18 to 28 carbon atoms.
2. Dialkyl esters according to claim 1, characterized in that $R_2$ contains 18 to 24 carbon atoms.
* * * * *